United States Patent [19]

Sterne

[11] 4,103,010
[45] Jul. 25, 1978

[54] (3-PIPERAZINOCARBONYLIMINO-QUANIDINO)-ISOXAZOLES

[75] Inventor: Jean-Jacques Sterne, Suresnes, France

[73] Assignee: Aron S.A.R.L., Suresnes, France

[21] Appl. No.: 834,976

[22] Filed: Sep. 20, 1977

Related U.S. Application Data

[63] Continuation-in-part of Ser. No. 646,928, Jan. 6, 1976.

[30] Foreign Application Priority Data

Jan. 16, 1975 [GB] United Kingdom ............... 1948/75

[51] Int. Cl.² .......................................... C07D 413/12
[52] U.S. Cl. ............................. 424/250; 260/307 H; 260/293.58; 544/137; 544/367
[58] Field of Search .................. 260/268 H; 424/250

[56] References Cited

U.S. PATENT DOCUMENTS 3,808,224  4/1974  Aron-Samuel .................. 260/307 G
3,950,333  4/1976  Durant et al. .................. 260/307 H Primary Examiner—Jose Tovar
Attorney, Agent, or Firm—Young & Thompson

[57] ABSTRACT

The present invention relates to compounds having the general formula:

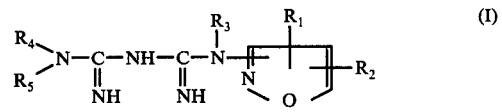

in which $R_1$ and $R_2$, which may be the same or different, represent each a hydrogen atom, a $C_1$–$C_6$ alkyl radical or a $C_3$–$C_6$ cycloalkyl radical; $R_3$ represents a hydrogen atom or a $C_1$–$C_4$ alkyl radical; $R_4$ and $R_5$, which may be the same or different, represent a hydrogen atom, a $C_1$–$C_6$ alkyl radical or, together with the nitrogen atom to which they are attached, form a pyrrolidino, piperidino, morpholino or piperazinyl radical optionally substituted with a $C_1$–$C_4$ alkyl radical, or a 4-hydroxypiperidino radical, and their pharmaceutically acceptable acid addition salts.

Said compounds are therapeutically useful for the control of the cardio-vascular system and of the blood pressure.

11 Claims, No Drawings

(3-PIPERAZINOCARBONYLIMINO-QUANIDINO)-ISOXAZOLES

The present application is a continuation in part of the U.S. Ser. No. 646,928 filed Jan. 6, 1976.

The present invention relates to new biguanides, to the process for their preparation and to their applications, particularly for therapeutic purposes.

The present invention relates to compounds having the general formula:

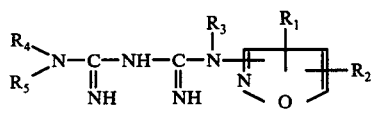

in which:

$R_1$ and $R_2$, which may be the same or different, represent each a hydrogen atom, a $C_1$-$C_6$ alkyl radical or a $C_3$-$C_6$ cycloalkyl radical;

$R_3$ represents a hydrogen atom or a $C_1$-$C_4$ alkyl radical; and $R_4$ and $R_5$, which may be the same or different, represent each a hydrogen atom, a $C_1$-$C_6$ alkyl radical or, together with the nitrogen atom to which they are attached, form a pyrrolidino, piperidino, morpholino or piperazinyl radical optionally substituted with a $C_1$-$C_4$ alkyl radical, or a 4-hydroxy-piperidino radical, and their pharmaceutically acceptable acid addition salts.

The acid addition salts may typically be those formed with hydrochloric, sulfuric, phosphoric, methane sulfonic, maleic, succinic, pamoic, acetic, fumaric, lactic, aspartic and citric acids.

The compounds of the formula (I) may be prepared by reacting a cyano-guanidine having the formula:

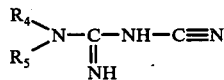

with an amino-isoxazole having the formula:

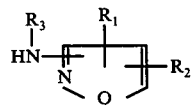

in which $R_1$, $R_2$, $R_3$, $R_4$ and $R_5$ have the above-defined meanings.

The reaction may be effected with or without solvent, the compound of the formula (III) being, or not, in salt form. For example, the cyano-guanidine (II) may be reacted with the hydrochloride of amino isoxazole (III) within an aqueous or organic solvent, with slight heating or at the refluxing temperature of the solvent.

The following examples are given to illustrate the preparation of the compounds of this invention.

EXAMPLE 1

In a 2 liter three-necked flask are added 370 g of 3-amino-5-methyl-isoxazole hydrochloride, 231 g of 1-cyanoguanidine and 500 ml of butanol. The temperature is gradually raised to the refluxing temperature of the solvent, at which level it is then maintained during 10 minutes. The reaction mixture is allowed to cool and, after incipient crystallization, is poured over 2 liters of butanol. After complete crystallization, the resulting material is filtered, the solid is washed with 300 ml of isopropanol. The solid is recrystallized from 1 liter 90% ethanol, to give 250 g of (5-methyl-isoxazol-3-yl)biguanide hydrochloride. M.p. (Kofler) = 210°-212° C. M.p. (cap.) = 195°-196° C with introduction at 185° C and heating at a rate of 2° C/minute.

EXAMPLE 2

In a reactor are added 4.9 g of 1-cyano-3-methyl-guanidine, 6.7 g of 3-amino-5-methyl-isoxazole hydrochloride and 1.3 ml of water. The reaction mixture is heated until dissolution is complete, after which the reaction is exothermal. After cooling, the reaction mixture is taken up into 30 ml water followed by 3 ml ammonia (d = 0.89). It is then extracted with 30 ml methylene chloride. After drying, treatment with carbon black and evaporation of the solvent, the residue is crystallized from absolute ethanol, to give 2.7 g of 1-methyl-5-(5-methyl-isoxazol-3-yl)-biguanide. M.p. (cap.) = 140° C followed by resolidification, then 150°-151° C with introduction at 140° C and heating at a rate of 2° C/minute.

In following Table I are tabulated the characteristics of the compounds of Examples 1 and 2 together with those of other compounds prepared in a way analogous to that described in Example 1. The melting points are those measured with a capillary tube, with introduction at 10° C above the expected melting point and heating at a rate of 2° C/minute.

TABLE I

| Example | $R_1$ | $R_2$ | $R_3$ | P* | $R_4$ | $R_5$ | Form | M.p.(° C) |
|---|---|---|---|---|---|---|---|---|
| 1 | H | 5-$CH_3$ | H | 3 | H | H | HCl | 195 – 196 |
|   |   |   |   |   |   |   | Base | 150 – 151 |
| 2 | H | 5-$CH_3$ | H | 3 | $CH_3$ | H | HCl | 169 – 171 |
| 3 | H | 5-$CH_3$ | H | 3 | $CH_3$ | $CH_3$ | HCl | 228 |
| 4 | H | 5-$C_2H_5$ | H | 3 | H | H | Base | 157 – 158 |
| 5 | H | 5-$C_4H_9$ | H | 3 | H | H | Base | 162 – 163 |
| 6 | H | 5-CH($CH_3$)$_2$ | H | 3 | H | H | Base | 178 |
| 7 | H | 5-$CH_3$ | $CH_3$ | 3 | H | H | HCl | 185 |
| 8 | 4-$CH_3$ | H | H | 3 | H | H | HCl | 211 |
| 9 | H | H | H | 3 | H | H | HCl | 206 – 207 |

TABLE I-continued

Structure: $R_4R_5N-C(=NH)-NH-C(=NH)-N(R_3)-$ [isoxazole ring with $R_1$, $R_2$ substituents, N at position 2, O at position 1]

| Example | $R_1$ | $R_2$ | $R_3$ | P* | $R_4$ | $R_5$ | Form | M.p.(° C) |
|---|---|---|---|---|---|---|---|---|
| 10 | 4-$CH_3$ | 5-$CH_3$ | $CH_3$ | 3 | H | H | HCl | 213 – 214 |
| 11 | 4-$CH_3$ | H | H | 3 | $CH_3$ | $CH_3$ | HCl | 191 |
| 12 | H | 5-(cyclopropyl) | H | 3 | H | H | Base | 161 |
| 13 | H | 5-$CH_3$ | H | 3 | $C_4H_9$ | H | HCl | 174 – 175 |
| 14 | 4-$C_2H_5$ | H | H | 3 | H | H | HCl | 202 |
| 15 | H | 5-(cyclohexyl) | H | 3 | H | H | HCl | 187 |
| 16 | H | 5-$CH_3$ | $C_2H_5$ | 3 | H | H | HCl | 160 |
| 17 | H | 5-$CH_3$ | H | 3 | —$(CH_2)_4$— | | HCl | 208 – 209 |
| 18 | H | 5-$CH_3$ | H | 3 | —$(CH_2)_5$— | | HCl | 213 –214 |
| 19 | H | 5-$CH_3$ | H | 3 | —$(CH_2)_2$—N($CH_3$)—$(CH_2)_2$— | | Base / 2HCl | 174 / 215 |
| 20 | H | 5-$CH_3$ | H | 3 | —$(CH_2)_2$—O—$(CH_2)_2$— | | HCl | 209 |
| 21 | H | 5-$CH_3$ | H | 3 | —$(CH_2)_2$—CH(OH)—$(CH_2)_2$— | | fumarate ½ $H_2O$ | 194 – 196 |
| 22 | 3-$CH_3$ | 5-$CH_3$ | H | 4 | H | H | HCl | 230 |
| 23 | 3-$CH_3$ | 5-$CH_3$ | H | 4 | $C_4H_9$ | H | HCl | 223 dec. |
| 24 | 3-$CH_3$ | 5-$CH_3$ | H | 4 | $CH_3$ | $CH_3$ | HCl | 258 dec. |
| 25 | 3-$CH_3$ | 4-$CH_3$ | H | 5 | H | H | HCl | 218 dec. |
| 26 | 3-$CH_3$ | 4-$CH_3$ | H | 5 | $C_4H_9$ | H | HCl | 161 – 162 |
| 27 | 3-$CH_3$ | 4-$CH_3$ | H | 5 | $CH_3$ | $CH_3$ | HCl | 204 – 205 |
| 28 | H | 5-$CH_3$ | H | 3 | —$(CH_2)_2$—N($C_3H_7$)—$(CH_2)_2$— | | 2 HCl | 238 |
| 29 | H | 4-$CH_3$ | H | 3 | —$(CH_2)_2$—N($CH_3$)—$(CH_2)_2$— | | Base | 135 – 136 |
| 30 | H | 5-$CH_3$ | H | 3 | —$(CH_2)_2$—N(H)—$(CH_2)_2$— | | 2$CH_3SO_3H$ | 224 |

*P = position of the biguanide radical on the isoxazole nucleus

Results of toxicological and pharmacological investigations demonstrating the useful activities of the compounds of the formula (I) that make them valuable for therapeutic purposes are reported below.

The data obtained on acute toxicity investigation in mice are set forth in Table II.

TABLE II

| Compound of Example | $LD_{50}$ (mg/kg) p.o. | $LD_{50}$ (mg/kg) i.v. |
|---|---|---|
| 1 | 700 | 115 |
| 2 | 900 | — |
| 3 | 800 | 140 |
| 4 | 500 | 45 |
| 5 | 600 | — |
| 6 | 200 | — |
| 7 | > 1000 | 70 |
| 8 | 300 | 70 |
| 9 | > 1000 | > 150 |
| 10 | > 500 | 100 |
| 11 | 300 | 40 |
| 13 | 250 | 35 |
| 14 | 500 | — |
| 16 | > 750 | — |
| 19 | 2000 | 100 |
| 20 | 750 | 100 |
| 22 | > 1500 | > 100 |
| 23 | > 750 | — |
| 24 | > 750 | — |
| 25 | 300 | 20 |
| 26 | 250 | 35 |
| 27 | 700 | — |
| 28 | 400 | — |
| 29 | > 1000 | — |
| 30 | > 1000 | — |

The compounds of the formula (I) are capable of modifying the accumulation of noradrenalin and particularly to inhibit the uptake of $^3H$ noradrenalin by the synaptosomes of a rat hypothalamus homogenate prepared according to Banerjee, Snyder and Mechoulam (J. Pharmacol. Exp. Ther., 194, 1, 74, 1975). This inhibition of the uptake of $^3H$ noradrenaline is a known property of various compounds having an activity on the central nervous system and/or on the sympathetic nervous system, particularly a hypotensive effect (J. Glowinski and J. Axelrod, effects of Drugs on the Disposition of $^3H$ norepinephrine in the Rat Brain, Pharmacological Reviews, Vol. 18, No. 1, Part I, 1966).

The results obtained are given in Table III. They are expressed as percent inhibition of the uptake with respect to the control test.

TABLE III

| Ultimate molar concentration of the compound | $5 \times 10^{-4}$ M | $5 \times 10^{-5}$ M | $5 \times 10^{-6}$ M |
|---|---|---|---|
| Compound | inhibition % | inhibition % | inhibition % |
| 1 | 64 | 31 | — |
| 2 | 53.6 | — | — |
| 3 | 47.9 | — | — |
| 4 | 52.7 | — | — |
| 5 | 69.5 | — | — |
| 6 | — | 54.6 | — |
| 7 | 48.1 | — | — |
| 8 | — | 55 | 36 |
| 9 | 68.6 | — | — |
| 10 | 19.5 | — | — |
| 11 | 60.1 | — | — |
| 13 | 63.1 | — | — |
| 14 | — | 61.8 | 46.5 |
| 16 | 37.9 | — | — |
| 19 | 53.8 | — | — |
| 20 | 46.6 | — | — |
| 23 | 51 | — | — |
| 24 | 28.4 | — | — |

TABLE III-continued

| Ultimate molar concentration of the compound Compound | $5 \times 10^{-4}$ M inhibition % | $5 \times 10^{-5}$ M inhibition % | $5 \times 10^{-6}$ M inhibition % |
| --- | --- | --- | --- |
| 25 | — | 45.5 | — |
| 26 | — | 39.6 | — |
| 27 | 38.1 | — | — |
| 28 | 60.2 | 20 | — |
| 29 | — | 65.8 | 30.8 |
| 30 | 51 | — | — |

The above results are confirmed by the results of an investigation of the action on the control of blood pressure. On oral administration of a dosage of 2 × 3 mg/kg of compound to Doca rats (Technique according to Green and co-workers, Am. J. Physiol., 1952, 170, p. 94) and to Grollman rats (Technique according to Grollman, Proc. Soc. Exp. Biol. Med., 1944, 57, p. 102), the percent decrease of the systolic blood pressure with respect to its original value is noted. The results obtained are given in Table IV.

TABLE IV

| Compound | Doca rats | Grollman rats |
| --- | --- | --- |
| 1 | 25 | 20 |
| 3 | — | 10 |
| 5 | 10 | — |
| 7 | 15 | — |
| 8 | 15 | 15 |
| 11 | 15 | — |
| 19 | 20 | 20 |
| 20 | — | 20 |
| 25 | 20 | — |
| 28 | 18 | 18 |
| 29 | 15 | 15 |
| 30 | 10 | — |

The compounds of the formula (I) and their therapeutically acceptable acid addition salts are therapeutically useful, particularly for the control of the cardiovascular system, for the regulation of the blood pressure, in particular for decreasing the blood pressure, and also as psychotropic agents.

Thus, the present invention includes also within its scope therapeutic compositions comprising, as active ingredient, a compound of the formula (I) or a therapeutically acceptable acid addition salt thereof, typically together with a pharmaceutically acceptable excipient.

The therapeutic compositions of this invention may be administered by the oral, parenteral or rectal routes.

Said compositions may be formulated typically as capsules, tablets, soft capsules, injectable ampoules, oral solutions and suppositories.

The daily dosage regimen may be from 10 mg to 1.8 g. When such compositions are formulated in unit dosage form, each unit dose may contain from 10 to 600 mg active ingredient.

An example of therapeutic composition is given below:

Capsules containing 25 mg active ingredient:
 Compound of Example 19 — 25 mg
 Aerosil — 2 mg
 Magnesium stearate — 2 mg
 Lactose, q.s. for one No. 3 capsule

Having now described my invention what I claim as new and desire to secure by Letters Patent is:

1. A compound selected from the group consisting of a compound having the formula:

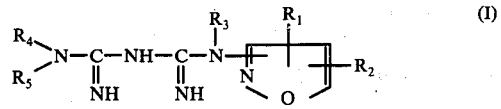

in which:
 $R_1$ and $R_2$, which may be the same or different, are each selected from the group consisting of hydrogen, $C_1 - C_6$ alkyl and $C_3 - C_6$ cycloalkyl;
 $R_3$ is selected from the group consisting of hydrogen and $C_1 - C_4$ alkyl;
 $R_4$ and $R_5$, taken together with the nitrogen atom to which they are attached, are selected from the group consisting of piperazinyl and $C_1 - C_4$ alkyl piperazinyl, and a pharmaceutically acceptable acid addition salt thereof.

2. A compound as claimed in claim 1, wherein $R_1$ is hydrogen, $R_2$ is methyl and $R_3$ is hydrogen.

3. A compound as claimed in claim 2, wherein $R_4$ and $R_5$ form a N-methyl piperazinyl radical.

4. A therapeutic composition for regulation of the blood pressure comprising a therapeutically effective quantity of a compound selected from the group consisting of a compound having the formula:

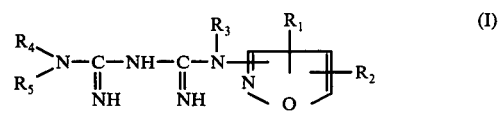

in which:
 $R_1$ and $R_2$, which may be the same or different, are each selected from the group consisting of hydrogen, $C_1 - C_6$ alkyl and $C_3 - C_6$ cycloalkyl;
 $R_3$ is selected from the group consisting of hydrogen and $C_1 - C_4$ alkyl;
 $R_4$ and $R_5$, taken together with the nitrogen atom to which they are attached, are selected from the group consisting of piperazinyl and $C_1 - C_4$ alkyl piperazinyl, and a pharmaceutically acceptable acid addition salt thereof, together with a pharmaceutical carrier.

5. A therapeutic composition as claimed in claim 4, formulated for oral, parenteral or rectal administration.

6. A therapeutic composition as claimed in claim 5, in unit dosage form.

7. A therapeutic composition as claimed in claim 6, wherein each dosage unit contains 10 to 600 mg of active ingredient.

8. A therapeutic process for decreasing the blood pressure of a patient requiring the same, comprising administering daily to said patient 10 mg to 1.8 g of a compound selected from the group consisting of a compound having the formula:

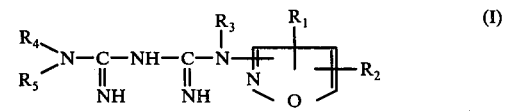

in which:
 $R_1$ and $R_2$, which may be the same or different, are each selected from the group consisting of hydrogen, $C_1 - C_6$ alkyl and $C_3 - C_6$ cycloalkyl;
 $R_3$ is selected from the group consisting of hydrogen and $C_1 - C_4$ alkyl;

$R_4$ and $R_5$, taken together with the nitrogen atom to which they are attached, are selected from the group consisting of piperazinyl and $C_1 - C_4$ alkyl piperazinyl, and a pharmaceutically acceptable acid addition salt thereof.

9. A compound selected from the group consisting of the compound having the formula

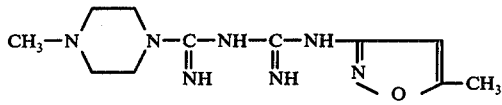

and a pharmaceutically acceptable acid addition salt thereof.

10. A therapeutic composition for regulation of the blood pressure comprising a therapeutically effective quantity of a compound selected from the group consisting of the compound having the formula

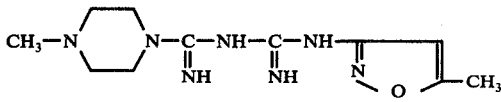

and a pharmaceutically acceptable acid addition salt thereof, together with a pharmaceutical carrier.

11. A therapeutic process for decreasing the blood pressure of a patient requiring the same, comprising administering daily to said patient 10 mg to 1.8 g of a compound selected from the group consisting of the compound having the formula:

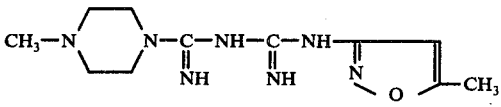

and a pharmaceutically acceptable acid addition salt thereof.

* * * * *